(12) United States Patent
Whittington

(10) Patent No.: US 10,689,821 B1
(45) Date of Patent: Jun. 23, 2020

(54) ALGAE SKIMMER AND DEBRIS REMOVAL SYSTEM

(71) Applicant: Peter Whittington, Oakland Park, FL (US)

(72) Inventor: Peter Whittington, Oakland Park, FL (US)

( * ) Notice: Subject to any disclaimer, the term of this patent is extended or adjusted under 35 U.S.C. 154(b) by 0 days.

(21) Appl. No.: 16/289,052

(22) Filed: Feb. 28, 2019

(51) Int. Cl.
| | |
|---|---|
| *E02B 15/04* | (2006.01) |
| *B63B 35/32* | (2006.01) |
| *C12N 1/12* | (2006.01) |
| *E02B 8/02* | (2006.01) |
| *B63B 25/00* | (2006.01) |
| *E02B 5/08* | (2006.01) |

(52) U.S. Cl.
CPC .............. *E02B 15/04* (2013.01); *B63B 35/32* (2013.01); *C12N 1/12* (2013.01); *B63B 25/004* (2013.01); *E02B 5/085* (2013.01); *E02B 8/023* (2013.01)

(58) Field of Classification Search
CPC ................................ E02B 15/04; B63B 35/32
USPC ............................................................ 405/60
See application file for complete search history.

(56) References Cited

U.S. PATENT DOCUMENTS

| | | | | |
|---|---|---|---|---|
| 3,731,813 A * | 5/1973 | Tipton | ................... | E02B 15/046 210/242.4 |
| 3,862,904 A * | 1/1975 | Weatherford | ......... | E02B 15/046 210/242.3 |
| 4,511,470 A * | 4/1985 | Ayroldi | ................. | E02B 15/106 210/242.3 |
| 5,207,901 A * | 5/1993 | Ravagnan | ............. | E02B 15/048 210/173 |
| 5,593,579 A * | 1/1997 | Reynolds | ............... | B01D 29/01 210/242.1 |
| 6,073,382 A * | 6/2000 | Willener | ................ | A01K 79/00 210/242.3 |
| 6,357,213 B1 * | 3/2002 | Dillingham | ............ | A01D 44/00 56/8 |
| 6,669,841 B2 * | 12/2003 | Morin | ..................... | B63B 35/32 210/170.05 |
| 7,045,058 B2 * | 5/2006 | Walczyk | ................. | B63B 35/32 210/170.05 |
| 7,452,462 B2 * | 11/2008 | Joliet | ..................... | B63B 35/32 210/170.05 |

(Continued)

FOREIGN PATENT DOCUMENTS

| | | | | |
|---|---|---|---|---|
| CN | 108951590 A | * | 12/2018 | |
| WO | WO-0027694 A1 | * | 5/2000 | ............. B63B 35/32 |

(Continued)

OTHER PUBLICATIONS

Wisconsin Department of Natural Resources (https://dnr.wi.gov/lakes/bluegreenalgae/).

(Continued)

*Primary Examiner* — Frederick L Lagman
(74) *Attorney, Agent, or Firm* — Laurence A. Greenberg; Werner H. Stemer; Ralph E. Locher

(57) ABSTRACT

An algae skimmer and debris removal system includes a water filter boat, a water and algae intake disposed on the water filter boat, a water filter disposed on the water filter boat downstream of the intake, a cleaned water outlet disposed on the water filter boat downstream of the filter and a debris collector disposed on the water filter boat for removing solid debris from the water. A debris compactor boat is detachably connected to the water filter boat and a compactor is disposed on the compactor boat for receiving the solid debris from the collector and for compacting the solid debris.

14 Claims, 5 Drawing Sheets

(56) References Cited

U.S. PATENT DOCUMENTS

| | | | | |
|---|---|---|---|---|
| 7,485,235 | B2 * | 2/2009 | Kellett | B63B 35/32 |
| | | | | 210/156 |
| 7,785,035 | B2 * | 8/2010 | Jarvinen | B63B 35/32 |
| | | | | 405/60 |
| 8,696,242 | B1 * | 4/2014 | Fesi | B63B 35/32 |
| | | | | 405/60 |
| 2015/0128838 | A1 * | 5/2015 | Bryan | C12M 47/02 |
| | | | | 114/61.1 |
| 2019/0063027 | A1 * | 2/2019 | Shurtleff | E02B 15/10 |

FOREIGN PATENT DOCUMENTS

| | | | | | |
|---|---|---|---|---|---|
| WO | WO-2007012696 | A1 * | 2/2007 | | B63B 35/32 |
| WO | WO-2012101304 | A1 * | 8/2012 | | B63B 35/32 |

OTHER PUBLICATIONS

EPA—U.S. Environmental Protection Agency, Nutrient Policy and Data, (https://www.epa.gov/nutrient-policy-data/control-and-treatment).

Engineers at the Ohio State University, "Water Filtration Technique Removes Dangerous Freshwater Algae Toxins" in ScienceDaily, Ohio State News by Harold Walker, Aug. 22, 2006, (https://news.osu.edu/water-filtration-technique-removes-dangerous-freshwater-algae-toxins/).

Article "A study of membrane filtration for the removal of cyanobacteria cells" in Journal of Water Supply: Research and Technology—AQUA 46(6), Dec. 1997—(abstract) (https://www.researchgate.net/publication/279908743_A_study_of_membrane_filtration_for_the_removal_of_cyanobacteria_cells).

* cited by examiner

ALGAE SKIMMER AND DEBRIS REMOVAL SYSTEM

BACKGROUND OF THE INVENTION

Field of the Invention

The invention relates to an algae skimmer and debris removal system for removing algae and debris from the surface of bodies of water.

Description of the Related Art

As stated on the website of the Wisconsin Department of Natural Resources (https://dnr.wi.gov/lakes/bluegreenalgae/), blue-green algae, also known as Cyanobacteria, are a group of photosynthetic bacteria which may also be blue, green, reddish-purple, or brown. Blue-green algae generally grow in lakes, ponds, and slow-moving streams when the water is warm and enriched with nutrients such as phosphorus or nitrogen. Blue-green algae can grow very quickly and most species are buoyant and will float to the surface, where they form scum layers or floating mats, which is referred to as a "blue-green algae bloom."

Blue-green algae causes discolored water, reduced light penetration, taste and odor problems, dissolved oxygen depletions during die-off, and toxin production. Blue-green algae blooms can reduce light penetration, which adversely affects aquatic organisms such as phytoplankton and aquatic plants as well as zooplankton and fish.

A blue-green algae bloom floating on the surface of a body of water should not be treated with a herbicide or algaecide since although it may kill the blue-green algae, toxins in the bloom will be released, resulting in toxins in the water.

According to the U.S. Environmental Protection Agency, Nutrient Policy and Data, (https://www.epa.gov/nutrient-policy-data/control-and-treatment) oil-spill skimmers have been used to remove Cyanobacteria blooms from surface scums formed especially in the later stages of a bloom. That practice may be coupled with the implementation of some coagulant or flocculant.

Engineers at the Ohio State University have used water filters combining activated carbon with three different commercially available membrane filters to remove Microcystis, a blue-green algae, as reported in an article entitled "Water Filtration Technique Removes Dangerous Freshwater Algae Toxins" in ScienceDaily, 5 Sep. 2006, (https://news.osu.edu/water-filtration-technique-removes-dangeroLis-freshwater-alaae-toxins/) reports that. Other filtration methods are known as well.

Another study has found that commercially available microfiltration (MF) and ultrafiltration (UF) flat sheet membranes, which differ with regard to their pore size, operated under both dead-end (DE) and cross-flow (CF) modes, are effective in removing Cyanobacterial cells (https://www.researchgate.net/publication/279908743_A_study_of_membrane_filtration_for_the_removal_of_cyanobacteria_cells).

However, none of the known systems permit rapid and large-scale skimming and filtration of blue-green algae.

BRIEF SUMMARY OF THE INVENTION

It is accordingly an object of the invention to provide an algae skimmer and debris removal system, which overcomes the hereinafore-mentioned disadvantages of the heretofore-known systems of this general type and which permit large bodies of water to be skimmed and filtered quickly and efficiently.

With the foregoing and other objects in view there is provided, in accordance with the invention, an algae skimmer and debris removal system, comprising a water filter boat, a water and algae intake disposed on the water filter boat, a water filter disposed on the water filter boat downstream of the intake, a cleaned water outlet disposed on the water filter boat downstream of the filter, a debris collector disposed on the water filter boat for removing solid debris from the water, a debris compactor boat being detachably connected to the water filter boat, and a compactor disposed on the compactor boat for receiving the solid debris from the collector and for compacting the solid debris. The water filter boat has at least one engine for propelling the water filter boat and towing the compactor boat, whereas the compactor boat is towed or pushed by the water filter boat. The system permits an efficient and speedy filtration of algae and removal of solid debris to be carried out.

In accordance with another feature of the invention, the water filter boat includes a frame on which the intake, the filter and the outlet are disposed. Pontoons support the frame and permit the water filter boat to float on the surface of a body of water. A housing, in which the filter is disposed, is supported on the frame. The water filter boat thus has a compact construction and yet is able to clean a large amount of water in a short period of time.

In accordance with an additional feature of the invention, the debris collector includes a crane or boom having a grabber for lifting the solid debris from the surface of the water and depositing the solid debris on the debris compactor boat. The crane or boom is rotatable about a turret and a driver's cab is mounted on the water filter boat for manual control of the crane or boom and the grabber. The crane or boom has pivot joints rotated by hydraulic mechanisms permitting the grabber to be easily manipulated by an operator.

In accordance with yet another feature of the invention, the debris compactor boat is an amphibious craft which has wheels permitting the debris compactor boat to be pulled or pushed onto dry land or a boat ramp. The debris compactor boat can therefore be easily pulled or pushed onto land and disconnected from the water filter boat, so that another compactor boat can be quickly connected and filtration and debris removal can continue with minimal down time.

In accordance with yet a further feature of the invention, the water and algae intake has a grill with gaps preventing solid debris from entering the water and algae intake. A screen with perforations can be used as an alternative or in addition to the grill.

In accordance with yet another feature of the invention, the water filter includes a plurality of identical filters or different filters, which may include at least one activated carbon filter and at least one microfiltration or ultrafiltration membrane. Such filters have been found to be effective in filtering algae, such as blue green algae.

In accordance with a concomitant feature of the invention, at least one pump is provided for suctioning water from the water intake, through the filter and out the water outlet.

Other features which are considered as characteristic for the invention are set forth in the appended claims.

Although the invention is illustrated and described herein as embodied in an algae skimmer and debris removal system, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of the specific embodiment when read in connection with the accompanying drawings.

DETAILED DESCRIPTION OF THE INVENTION

Figure 1:
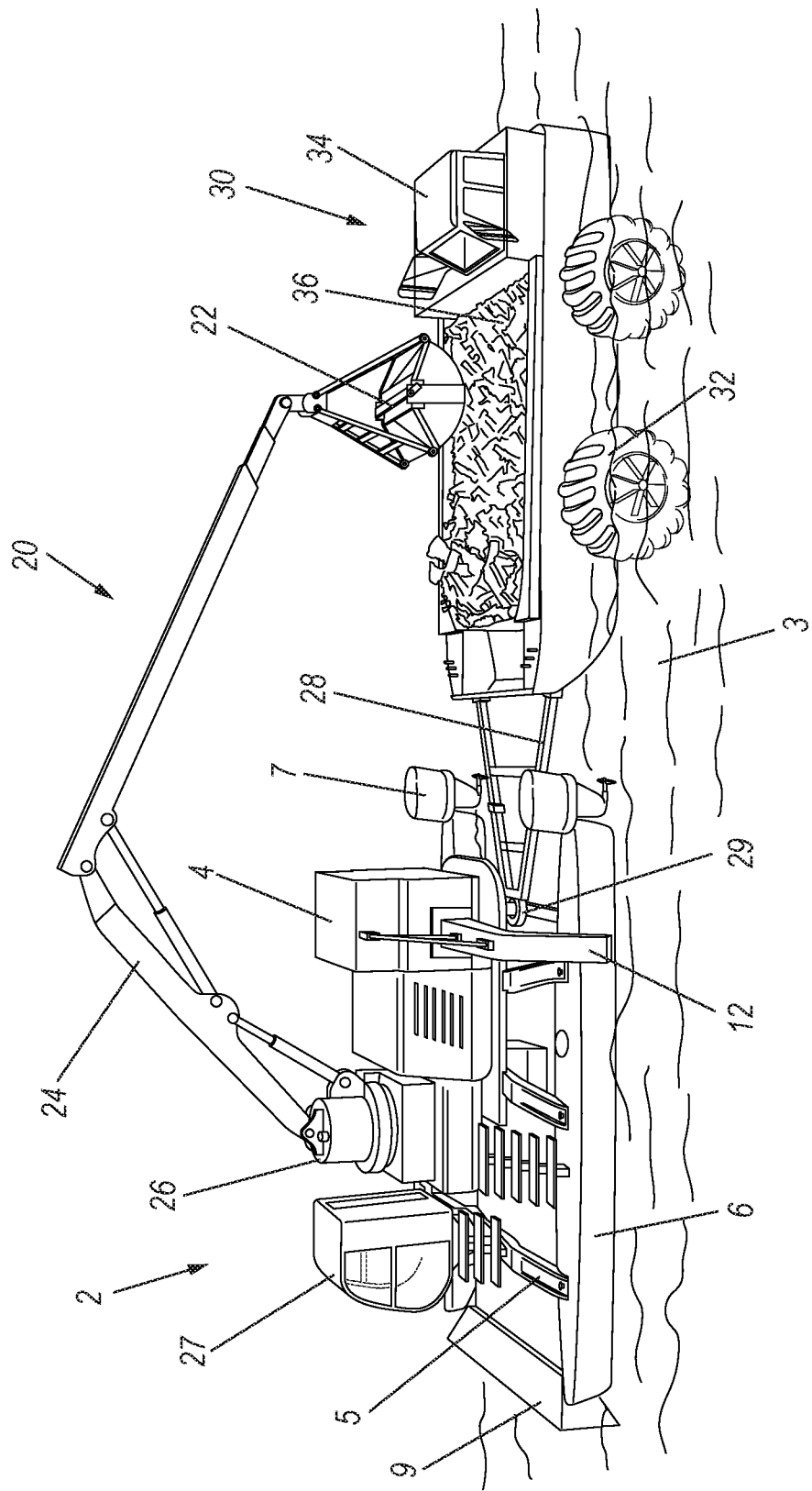
FIG. 1 is a diagrammatic, perspective view of a system including an over-sized water filter boat and a debris or garbage compactor boat floating on a body of water.

Referring now to the figures of the drawing in detail and first, particularly, to FIG. 1 thereof, there is seen an over-sized water filter boat 2 towing a debris or garbage compactor boat 30 floating on a body of water 3. The water filter boat 2 has a housing 4 supported on a frame 5 which in turn rests on pontoons 6 permitting the system to be used on the water. However, the debris or garbage compactor boat 30 also has wheels 32 permitting the compactor boat to be pulled or pushed onto dry land or a boat ramp as an amphibious craft. A trash compactor 34 is disposed on the compactor boat 30.

The body of water 3 is generally a large lake, other inland body of water or coastal water. The combined water filter boat 2 towing the debris or garbage compactor boat 30 is powered by two outboard engines 7 so as to move along the body of water 3 in parallel and adjacent rows or paths, similar to the rows or paths traversed by a lawn mover on land.

Figure 2:
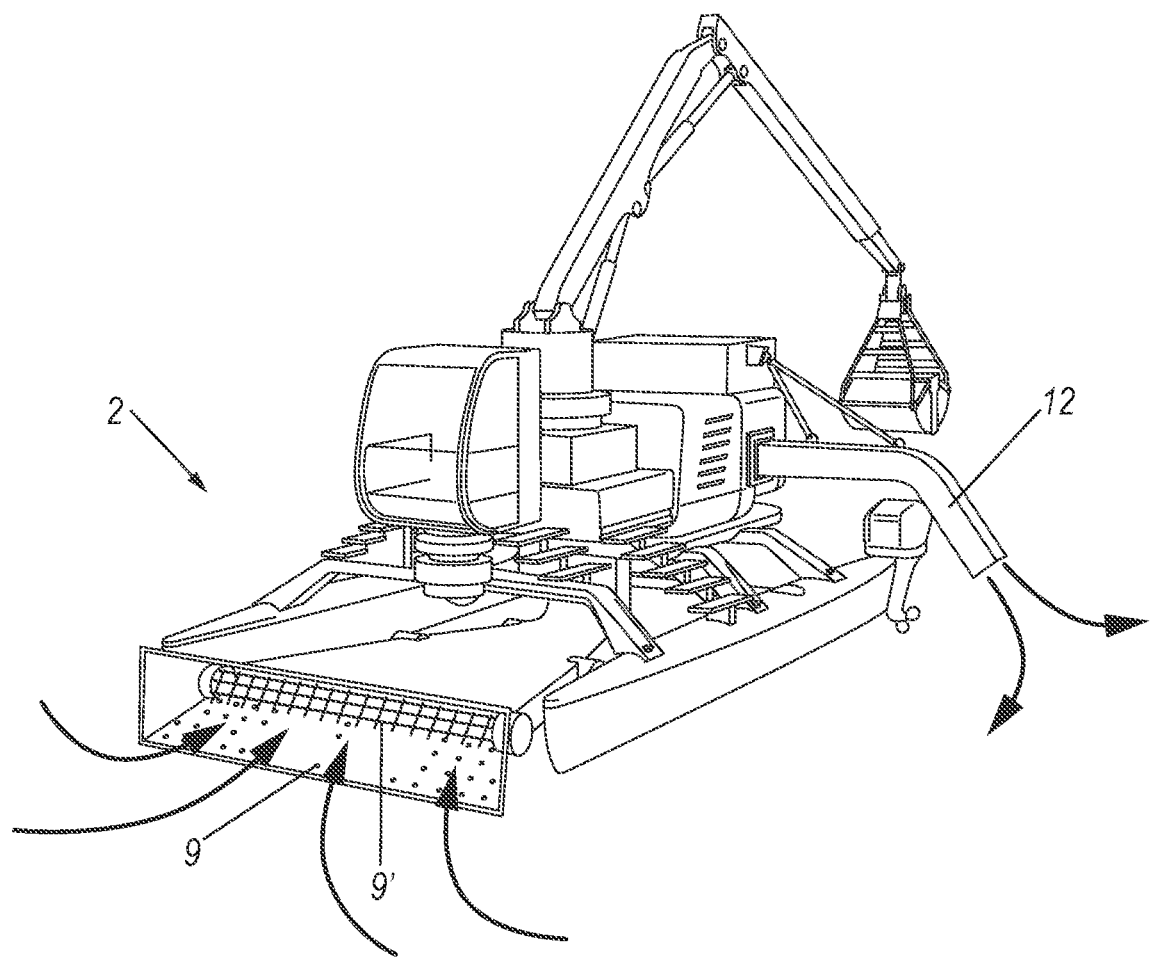
FIG. 2 is a front-perspective view of the water filter boat indicating an inflow and an outflow of water.
Figure 3:
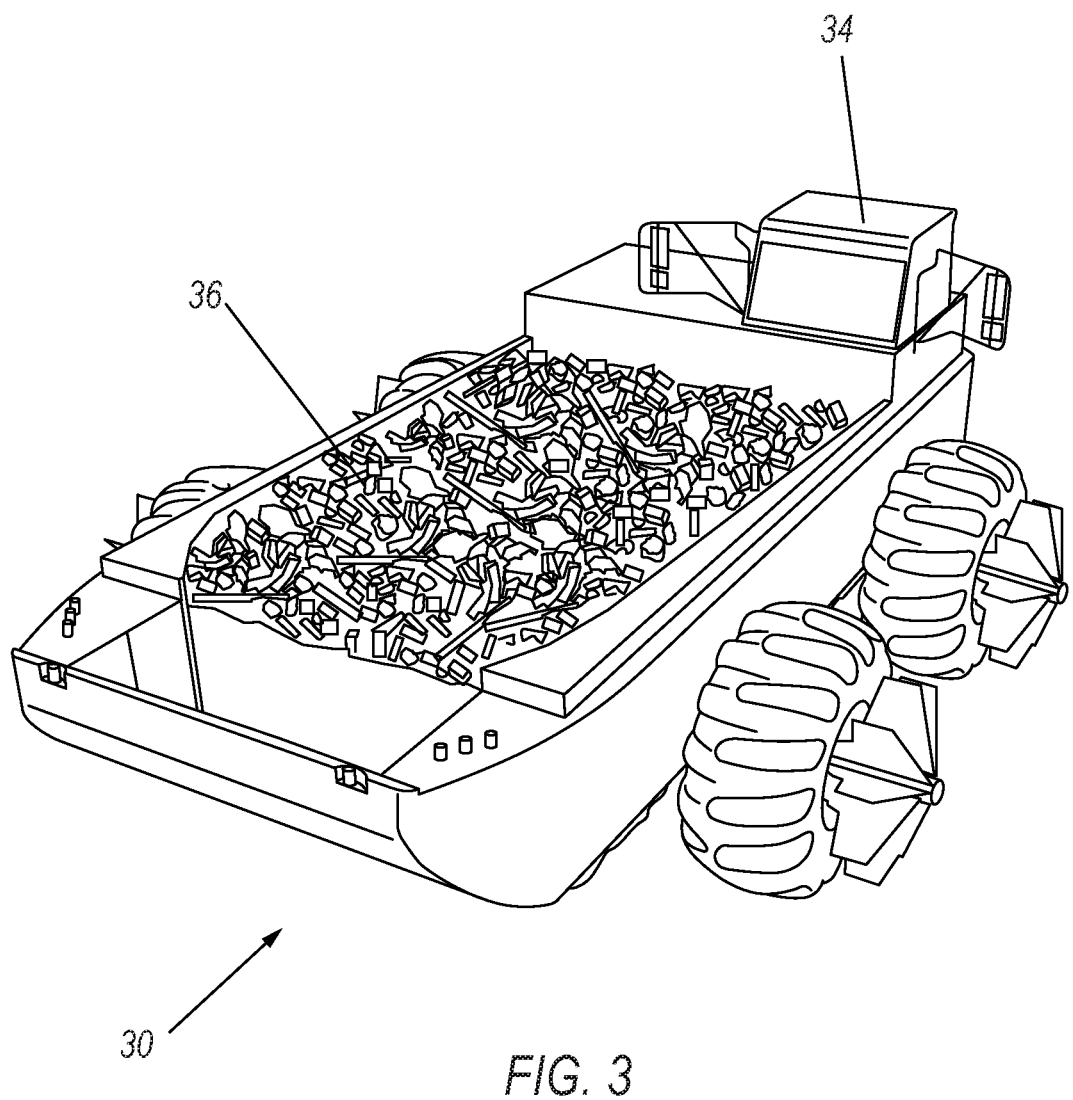
FIG. 3 is a front-perspective view of the amphibious debris or garbage compactor boat.

The water 3 containing algae is suctioned into a water intake 9 in the direction of the inwardly-pointing arrows in FIG. 2 and is fed to a water filter 14 disposed within the housing 4. The water intake 9 has pivots at the right and left and a grill with plates 9' having gaps therebetween preventing solid debris from entering the water intake 9. The plates are enlarged in the illustration for clarity. A screen with perforations could be used instead of or in addition to the plates. After filtration by the water filter 14 to remove the algae, the cleaned water is pumped out again in the direction of the outwardly-pointing arrows in FIG. 2 though a clean water outlet 12. Further details regarding the filtering operation will be described below with reference to FIG. 4.

Figure 4:
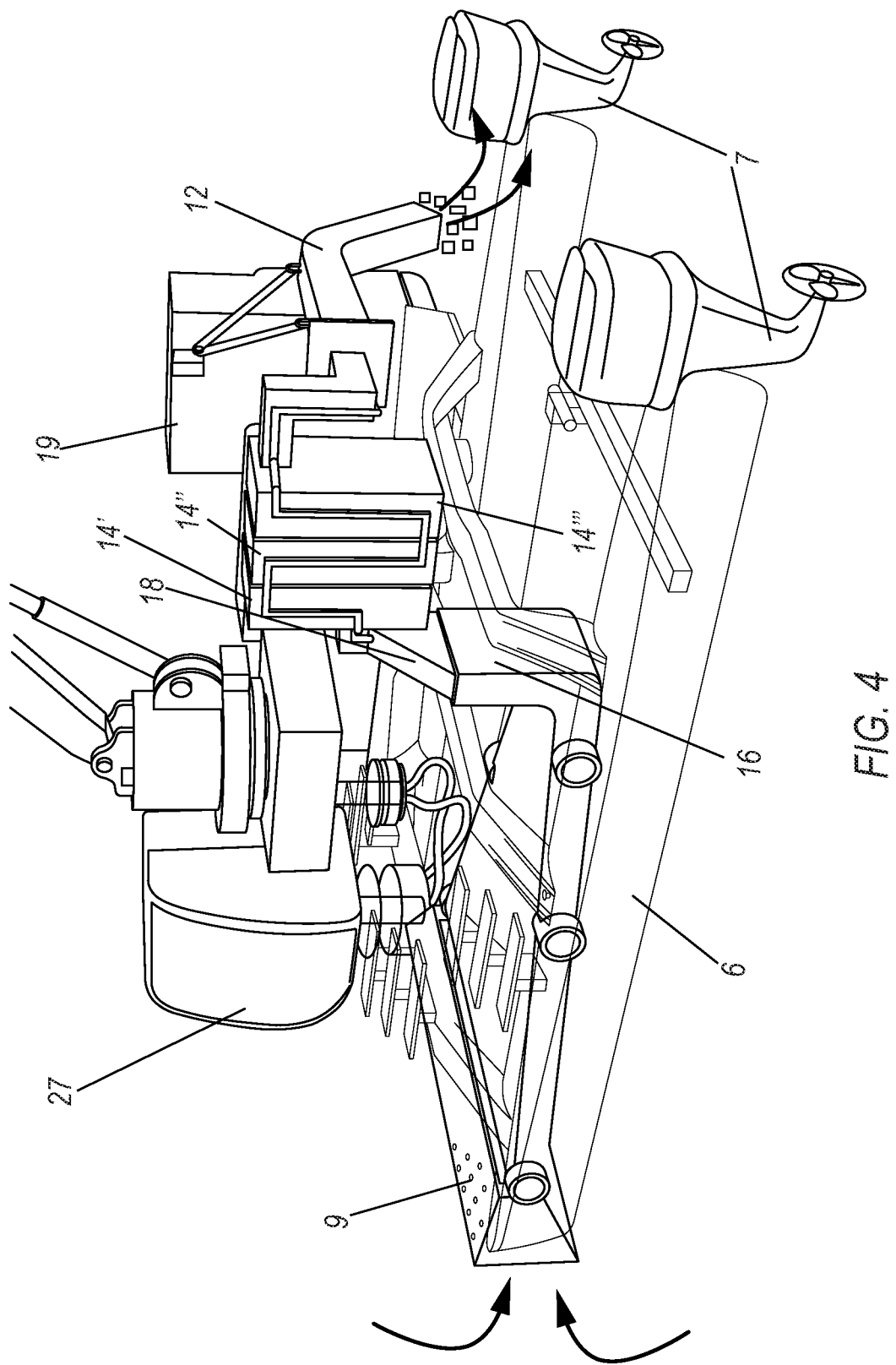
FIG. 4 is a side-perspective view of the water filter boat with the housing removed to show components of the water filter boat.

FIG. 4 shows that the filter boat 2 is equipped with the above-mentioned water intake 9 being carried by the frame 5 on the pontoons 6. The surface water and the algae is suctioned by a vacuum pump 16 through the gaps or perforations in the grill or screen so that no large pieces of garbage or debris are sucked in. The surface water and the algae is then fed through a channel 18 to three consecutive filters 14', 14'', 14''' which trap the algae. The filters may include an activated carbon filter and different commercially available membrane filters, such as microfiltration (MF) and ultrafiltration (UF) membranes. The water from which the algae has been removed is finally ejected through the water outlet 12 in the form of a pipe back onto the body of water as shown by the arrows in FIG. 4. An additional pump 19 may be provided between the filter 14 and the water outlet 12.

The garbage in the form of solid debris which is left behind after filtering the algae out of the water is placed into the compactor boat 30 by a debris collector 20. The debris collector 20 may include a clam shell grabber 22 disposed at the end of a crane or boom 24 which lifts the debris. The crane or boom 24 is rotatable through 360° on a turret 26 having a drive motor and manual controls. The grabber 22 deposits the debris 36 into the compactor boat 30. The debris could also be scooped into the compactor boat by brushes or blades rotating about a transverse shaft at the bow or stern of the compactor boat, like the wheel of a paddle boat. The debris could further be swept into the compactor boat by paddles or doors pivotable at the port and starboard bow or stern of the boat. Finally, a shovel such as is used on a front loader may be used at the bow or stern of the compactor boat. A cab 27 for a driver who operates the system is disposed next to the turret 26.

The compactor boat 30 has an A-frame 28 which is detachably connected to a ball hitch 29 on the water filter boat 2. The compactor 34 of the amphibious debris or garbage compactor boat 30 compacts the debris or garbage 36 to as to permit the largest possible amount of garbage to be loaded and compacted onto the compactor boat before it is rolled onto solid land, a beach or a boat ramp, disconnected from the water filter boat 2 and taken to a waste disposal or recycling plant. While one compactor boat 30 is being wheeled away, another compactor boat 30 can be attached to the water filter boat 2 so that practically continuous operation of the system is possible.

Figure 5:
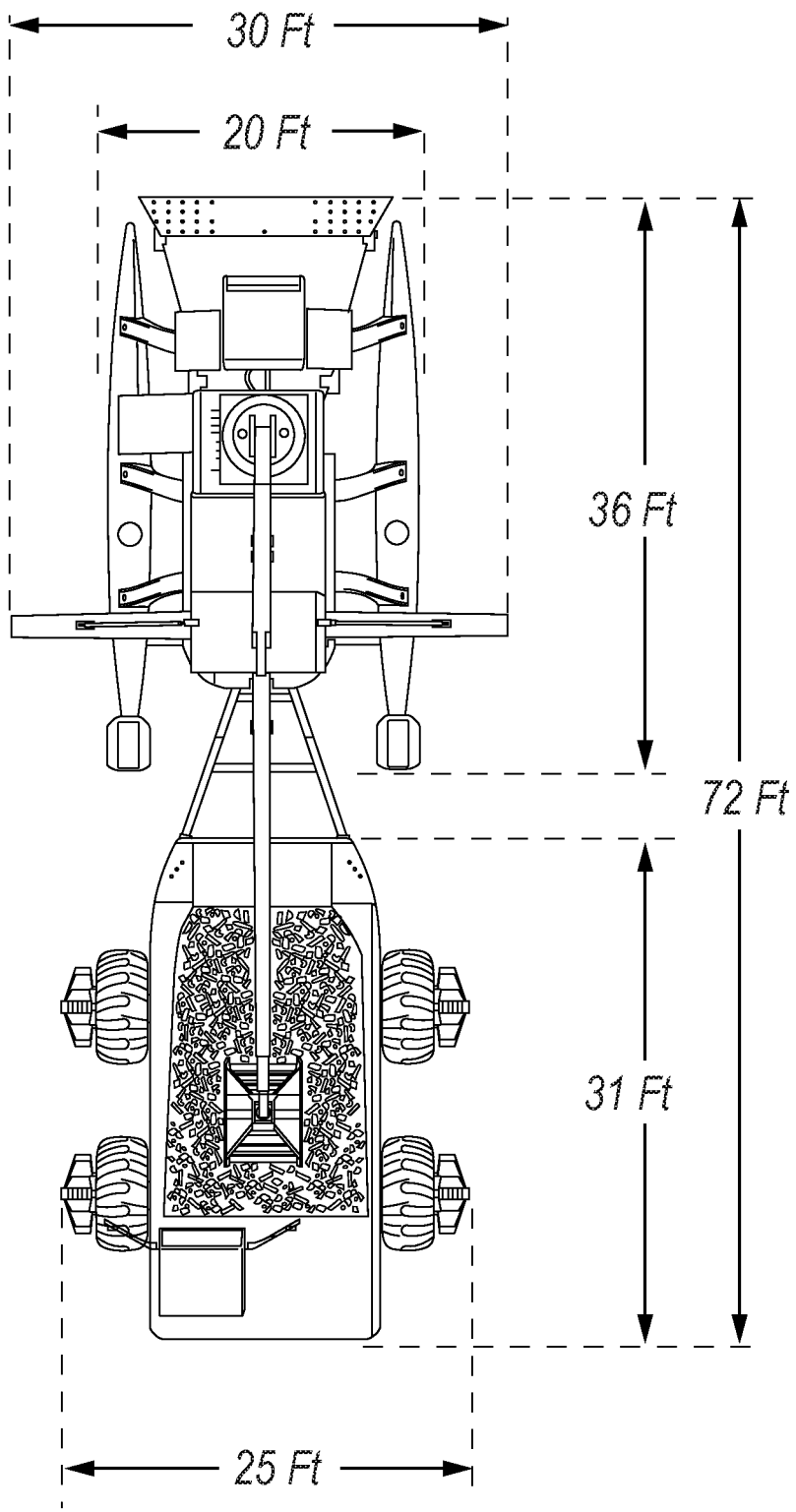
FIG. 5 is a top-plan view of the water filter boat and the debris or garbage compactor boat showing dimensions thereof.

Possible dimensions of the system are shown in FIG. 5 but are not intended to be limiting. Smaller systems for smaller bodies of water or larger systems for larger bodies of water may, of course, be used.

The invention claimed is:

1. An algae skimmer and debris removal system, comprising:
    a water filter boat;
    a water and algae intake disposed on said water filter boat;
    a water filter disposed on said water filter boat downstream of said intake;
    a cleaned water outlet disposed on said water filter boat downstream of said filter;
    a debris collector disposed on said water filter boat for removing solid debris from water;
    a debris compactor boat being an amphibious craft detachably connected to said water filter boat; and
    a compactor disposed on said compactor boat for receiving the solid debris from said collector and for compacting the solid debris.

2. The system according to claim 1, wherein said water filter boat includes a frame on which said intake, said filter and said outlet are disposed.

3. The system according to claim 2, which further comprises pontoons supporting said frame and permitting said water filter boat to float on a surface of a body of water.

4. The system according to claim 2, which further comprises a housing supported on said frame.

5. The system according to claim 1, wherein said debris compactor boat has wheels permitting said debris compactor boat to be pulled or pushed onto dry land or a boat ramp.

6. The system according to claim 1, wherein said water and algae intake has a grill with gaps preventing solid debris from entering said water and algae intake.

7. The system according to claim 1, wherein said water filter includes a plurality of identical filters (14', 14", 14'").

8. The system according to claim 1, wherein said water filter includes a plurality of different filters.

9. The system according to claim 8, wherein said plurality of different filters includes at least one activated carbon filter and at least one microfiltration or ultrafiltration membrane.

10. The system according to claim 1, which further comprises a pump for suctioning water from said water intake, through said filter and out said water outlet.

11. The system according to claim 1, wherein said water filter boat has at least one engine for propelling said water filter boat and towing said compactor boat.

12. An algae skimmer and debris removal system, comprising:

a water filter boat;

a water and algae intake disposed on said water filter boat;

a water filter disposed on said water filter boat downstream of said intake;

a cleaned water outlet disposed on said water filter boat downstream of said filter;

a debris collector disposed on said water filter boat for removing solid debris from water;

a debris compactor boat being detachably connected to said water filter boat; and a compactor disposed on said compactor boat for receiving the solid debris from said collector and for compacting the solid debris;

said debris collector including a crane or boom having a grabber for lifting the solid debris from the surface of the water and depositing the solid debris on said debris compactor boat.

13. The system according to claim 12, wherein said crane or boom is rotatable about a turret.

14. The system according to claim 12, which further comprises a driver's cab mounted on said water filter boat for manual control of said crane or boom and said grabber.

\* \* \* \* \*